United States Patent
Weissler et al.

(10) Patent No.: US 10,054,651 B2
(45) Date of Patent: Aug. 21, 2018

(54) DATA DETECTION TIMESTAMP DEVICE FOR USE IN COMBINATION WITH AN MRI APPARATUS AND A NUCLEAR IMAGING (PET OR SPECT) DEVICE

(71) Applicant: KONINKLIJKE PHILIPS N.V., Eindhoven (NL)

(72) Inventors: Bjoern Weissler, Aachen (DE); Manfred Bruno Zinke, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1046 days.

(21) Appl. No.: 14/374,926

(22) PCT Filed: Feb. 6, 2013

(86) PCT No.: PCT/IB2013/050981
§ 371 (c)(1),
(2) Date: Jul. 28, 2014

(87) PCT Pub. No.: WO2013/118060
PCT Pub. Date: Aug. 15, 2013

(65) Prior Publication Data
US 2015/0002150 A1 Jan. 1, 2015

Related U.S. Application Data

(60) Provisional application No. 61/596,778, filed on Feb. 9, 2012.

(51) Int. Cl.
*A61B 5/055* (2006.01)
*G01R 33/48* (2006.01)
*A61B 6/03* (2006.01)
*A61B 6/00* (2006.01)
*A61B 5/00* (2006.01)

(52) U.S. Cl.
CPC .......... *G01R 33/481* (2013.01); *A61B 5/0035* (2013.01); *A61B 5/055* (2013.01); *A61B 6/037* (2013.01); *A61B 6/4417* (2013.01); *A61B 6/5247* (2013.01)

(58) Field of Classification Search
USPC .................. 324/300–322; 600/407–435; 382/128–131; 378/4; 250/370.09
See application file for complete search history.

(56) References Cited

U.S. PATENT DOCUMENTS 7,180,074 B1 * 2/2007 Crosetto ............... G01T 1/1611
250/370.09
7,667,457 B2 2/2010 Linz et al.
(Continued)

FOREIGN PATENT DOCUMENTS

WO 02082112 A1 10/2002
WO 2006111869 A2 10/2006

*Primary Examiner* — Melissa Koval
*Assistant Examiner* — Tiffany Fetzner

(57) ABSTRACT

A data detection device is used in combination with a magnetic resonance imaging (MRI) apparatus. A magnetic field detection unit (34) serves to detect a temporally varying magnetic field generated by the MRI apparatus, and a timestamping unit (35) generates magnetic field detection timestamps in dependence of the detected temporally varying magnetic field. This allows determining a temporal relation to acquired MRI data.

13 Claims, 5 Drawing Sheets

(56) References Cited

U.S. PATENT DOCUMENTS

| | | | |
|---|---|---|---|
| 8,170,302 B1* | 5/2012 | Gleason | A61B 6/037 378/4 |
| 8,938,280 B2 | 1/2015 | Harvey | |
| 9,167,979 B2* | 10/2015 | Skidmore | A61B 5/04009 |
| 2007/0102641 A1 | 5/2007 | Schmand et al. | |
| 2008/0317313 A1* | 12/2008 | Goddard | A61B 5/721 382/131 |
| 2009/0108206 A1 | 4/2009 | Breuer et al. | |
| 2009/0149736 A1* | 6/2009 | Skidmore | A61B 5/04009 600/421 |
| 2010/0219820 A1* | 9/2010 | Skidmore | A61B 5/04009 324/247 |
| 2011/0092802 A1 | 4/2011 | Steckner | |
| 2011/0196228 A1 | 8/2011 | Cho et al. | |
| 2011/0257509 A1 | 10/2011 | Olsen et al. | |
| 2012/0106814 A1* | 5/2012 | Gleason | A61B 6/037 382/131 |
| 2015/0002150 A1* | 1/2015 | Weissler | A61B 6/037 324/309 |

* cited by examiner

DATA DETECTION TIMESTAMP DEVICE FOR USE IN COMBINATION WITH AN MRI APPARATUS AND A NUCLEAR IMAGING (PET OR SPECT) DEVICE

CROSS REFERENCE TO RELATED APPLICATIONS

This application is a national filing of PCT application Ser. No. PCT/IB2013/050981, filed Feb. 6, 2013, published as WO 2013/118060 A1 on Aug. 15, 2013, which claims the benefit of U.S. provisional application Ser. No. 61/596,778 filed Feb. 9, 2012, which is incorporated herein by reference.

FIELD OF THE INVENTION

The invention relates to a data detection device for use in combination with a magnetic resonance imaging (MRI) apparatus as well as to a corresponding data detection method and data detection computer program. The invention relates further to an imaging apparatus as well as to a corresponding imaging method and imaging computer program.

BACKGROUND OF THE INVENTION

In recent years, there has been a trend towards the combination of different medical imaging modalities for improved diagnosis. For example, the integration of biochemical or metabolic imaging provided by positron emission tomography (PET) and anatomical imaging provided by computed tomography (CT) has proven itself as a standard clinical tool. However, the use of CT in combination with PET has its limitations, such as notable irradiation (X-ray) dose and reduced soft tissue contrast compared to magnetic resonance imaging (MRI). For this reason, MRI is now considered to be an improved alternative to CT. Moreover, the combination of PET and MRI has the potential to offer truly simultaneous acquisition of PET and MRI data. This allows for simultaneous dynamic studies of different parameters, such as diffusion and perfusion, to gain new diagnostic information. In addition, it also enables an enhanced PET image reconstruction, for example, by correcting the acquired PET data for the effects of patient movements, because global and local motion of a body can be tracked efficiently by means of MRI. However, in order to benefit from the combination of two different medical imaging modalities, such as PET and MRI, one must be able to temporally relate the acquired data to each other.

SUMMARY OF THE INVENTION

It is regarded as being an object of the present invention to provide a data detection device for use in combination with a magnetic resonance imaging (MRI) apparatus, which allows determining a temporal relation to acquired MRI data, as well as a corresponding data detection method and data detection computer program. It is regarded as being a further object of the present invention to provide an imaging apparatus as well as a corresponding imaging method and imaging computer program.

In a first aspect of the present invention, a data detection device for use in combination with a magnetic resonance imaging (MRI) apparatus is presented, wherein the data detection device comprises:

a magnetic field detection unit for detecting a temporally varying magnetic field generated by the MRI apparatus, and a timestamping unit for generating magnetic field detection timestamps in dependence of the detected temporally varying magnetic field.

As will be described in more detail with reference to the embodiments, magnetic resonance imaging (MRI) is based on the use of three kinds of magnetic fields with completely different frequencies: (i) a strong, uniform, static magnetic field $B_0$; (ii) switched magnetic field gradients of low frequencies (which typically vary in the kHz-range), and; (iii) a pulse RF magnetic field $B_1$ (with a typical frequency in the range of about 100 Mhz). The temporal variations of the two latter magnetic fields inherently provide information about the times at which the MRI apparatus acquires MRI data (in the following also called "MRI acquisition timing"). By detecting such a temporally varying magnetic field generated by the MRI apparatus and by generating magnetic field detection timestamps in dependence of the detected temporally varying magnetic field, the data detection device can therefore determine, in a relatively simple manner, and, in particular, without the need for a special, dedicated interface between the data detection device and the MRI apparatus, a temporal relation to the acquired MRI data.

It is preferred that the magnetic field detection unit comprises at least one coil for providing electric currents induced by temporal variations of the temporally varying magnetic field, and a signal providing unit for providing signals in dependence of the provided electric currents, wherein the timestamping unit is adapted to generate the magnetic field detection timestamps in dependence of the provided signals.

Using the principle of electromagnetic induction, the temporally varying magnetic field generated by the MRI apparatus can be easily and efficiently detected. This also requires only very few additional electronic components to be added to the data detection device, and, therefore, provides a comparably cheap solution. Moreover, because the data detection device and the MRI apparatus can be galvanically separated, such a solution is also particularly safe. In addition, since the provided electric currents are induced by temporal variations of the temporally varying magnetic field, and since the MRI acquisition timing is manifested, in particular, in the temporal variations of the temporally varying magnetic field, the generated magnetic field detection timestamps can provide a meaningful temporal relation to the acquired MRI data.

In a preferred embodiment, the magnetic field detection unit further comprises a signal comparison unit for comparing the provided signals to a specified signal threshold, wherein the timestamping unit is adapted to generate the magnetic field detection timestamps when the provided signals cross the specified signal threshold.

By comparing the provided signals, which depend on the provided electric currents induced by the temporal variations of the temporally varying magnetic field, to a specified signal threshold, and by generating the magnetic field detection timestamps when the provided signals cross the specified signal threshold, the temporal variations of the temporally varying magnetic field can be easily determined.

It is preferred that the magnetic field detection unit is adapted to enable an adjustment of the sensitivity of detecting the temporally varying magnetic field.

As will be described in more detail with reference to the embodiments, the temporally varying magnetic field generated by the MRI apparatus varies not only with time but may also vary with position in space. For a reliable detection, it is therefore preferred that the sensitivity of detecting the temporally varying magnetic field can be adapted to fit the respective circumstances, e.g., the position and/or orientation of the data detection device relative to the temporally varying magnetic field. In a preferred embodiment, this may be realized by the signal comparison unit being adapted to enable an adjustment of the specified signal threshold.

It is also preferred that the data detection device further comprises a printed circuit board (PCB), wherein the at least one coil is made substantially from PCB traces or comprises an air-core inductor.

In particular by making the at least one coil substantially from PCB traces on a printed circuit board, the at least one coil can be manufactured in a particularily cheap and simple manner.

It is preferred that the magnetic field detection unit comprises three coils that are arranged to be perpendicular to each other.

By using information provided by the three perpendicularly arranged coils, the position and/or orientation of the data detection device relative to the temporally varying magnetic field may be determined.

It is also preferred that the temporally varying magnetic field to be detected is a switched magnetic field gradient generated by the MRI apparatus.

It is preferred that the data detection device further comprises a radio frequency shield for shielding the magnetic field detection unit from a pulse radio frequency (RF) magnetic field $B_1$ generated by the MRI apparatus.

This configuration ensures that the magnetic field detection unit is not influenced or disturbed by the pulse RF magnetic field $B_1$.

It is further preferred that the timestamping unit is adapted to generate the magnetic field detection timestamps in accordance with a common time base that is also utilized for generating data timestamps for data detected by the data detection device.

It is preferred that the data detection device is a nuclear data detection device, in particular, a positron emission tomography (PET) data detection device or a single photon emission computed tomography (SPECT) data detection device.

In a further aspect of the present invention, an imaging apparatus is presented.

In a further aspect of the present invention, a data detection method for use in combination with a magnetic resonance imaging (MRI) method is presented, wherein the data detection method comprises:

detecting a temporally varying magnetic field generated by the MRI method, by a magnetic field detection unit, and generating magnetic field detection timestamps in dependence of the detected temporally varying magnetic field, by a timestamping unit.

In a further aspect of the present invention, an imaging method is presented.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
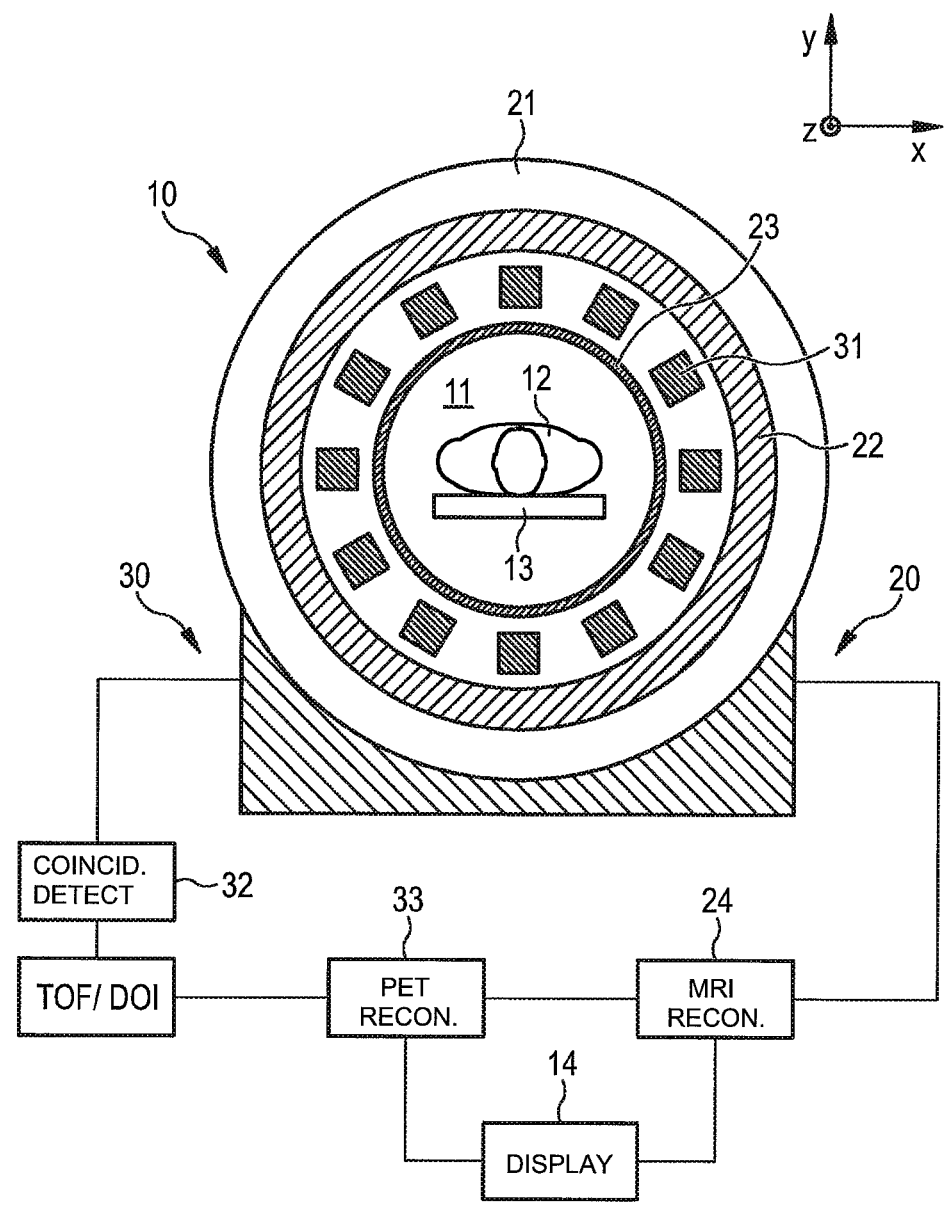
FIG. 1 shows schematically and exemplarily an embodiment of an imaging apparatus.

FIG. 1 shows schematically and exemplarily an embodiment of an imaging apparatus 10 comprising a magnetic resonance imaging (MRI) apparatus 20 and a positron emission tomography (PET) apparatus 30. The imaging apparatus 10 is capable of acquiring both MRI data and PET data, for example, from spatial areas of an imaging region 11 that are at least partially overlapping or spatially adjacent.

The MRI apparatus 20 comprises a main magnet 21 that serves to generate a strong, uniform, static magnetic field $B_0$ through the imaging region 11 (along the z direction, by convention). The main magnet 21 may be an annular magnet or a bore-type magnet. Moreover, the main magnet 21 may be superconducting or resistive in nature; in the former case, it is typically disposed in a cryogenic devar or other cooling system (not shown). The MRI apparatus 20 also comprises magnetic field gradient coils 22 that serve to superimpose switched magnetic field gradients in the x, y, and z directions on the static magnetic field $B_0$. In addition, the MRI apparatus 20 comprises a radio frequency excitation and reception system. The radio frequency excitation and reception system includes at least one component, such as an illustrated RF coil 23, that can be energized at a suitable radio frequency to generate a pulse RF magnetic field $B_1$ that excites magnetic resonance (MR) in an imaging subject 12, for example, a human patient, disposed on a table 13 in the imaging region 11. The RF coil 23 can also operate as an RF receiver to receive or detect the MR signals emanating from the imaging region 11 after RF excitation. In some embodiments, different coils are used for the excitation and reception operations. For example, the built-in RF coil 23 may be used to excite magnetic resonance and a different, local coil or dedicated receive coil (not shown) may be positioned over, on, or close to the imaging subject 12 in the imaging region 11 to detect magnetic resonance. It is possible that the MRI apparatus 20 is configurable in different ways using different combinations of built-in coils, local coils, or both.

In MRI, the nuclear spins of the tissue of the imaging subject 12 are aligned by the static magnetic field $B_0$ generated by the main magnet 21 and are excited by the pulse RF magnetic field $B_1$ generated, for example, by the RF coil 23. The resulting MR signals are exposed to the switched magnetic field gradients generated by the magnetic field gradient coils 22 to "spatially encode" the MR signals by creating a signature resonance frequency at each location in the imaging subject 12. The relative order and the specific temporal variations of the pulse RF magnetic field $B_1$ and of the switched magnetic field gradients are typically selectable according to need from a number of predefined "MR pulse sequences" that each show different effects on the characteristics of the resulting MRI images. The spatially encoded MR signals acquired, for example, by the RF coil 23 are temporarily stored in an MRI data storage unit (not shown) for later use, for example, in MRI image reconstruction. To this end, the MRI apparatus 20 comprises an MRI image reconstruction unit 24 that reconstructs the MRI data into a reconstructed MRI image using an image reconstruction algorithm that is suitably adapted to the spatial encoding used in acquiring the MRI data. For example, a Fourier Transform reconstruction algorithm may be suitably used for reconstructing Cartesian encoded MRI data. The reconstructed MRI image is suitably displayed on a display unit 14, for example, by means of a suitable two- or three-dimensional rendering method, or may be otherwise processed.

The PET apparatus 30 comprises a number of positron emission tomography (PET) data detection devices 31 that encircle the imaging region 11. Here, twelve PET data detection devices 31, illustrated as densely shaded boxes, are positioned on a circle between the magnetic field gradient coils 22 and the RF coil 23. In some embodiments, the PET data detection devices 31 can also be positioned in corresponding recesses in the magnetic field gradient coils 22 or they can be otherwise positioned in a most suitable manner.

In PET imaging, a radiopharmaceutical is administered to the imaging subject 12, in which the radioactive decay events of the radiopharmaceutical produce positrons. Each positron interacts with an electron to produce a positron-electron annihilation event that emits two oppositely directed 511 keV gamma rays. The PET data detection devices 31 are adapted to detect the 511 keV gamma rays that are emitted by the positron-electron annihilation events. Two substantially simultaneous 511 keV gamma ray detection events are thereby presumed to have originated from the same positron-electron annihilation event, which is located somewhere along a "line of response" (LOR) connecting the two substantially simultaneous 511 keV gamma ray detection events. This line of response is sometimes also called a projection or a ray, and the acquired PET data are referred to as projection data.

The constitution of the PET data detection devices 31 is not shown in detail in FIG. 1. However, in an embodiment, these devices may each include a pixelated array of scintillation crystals optically coupled to a light guide which propagates photons emitted by the scintillation crystals upon incidence of gamma rays to an array of sensor tiles. Each sensor tile typically includes an array of silicon photomultipliers (SiPMs) which, in turn, each include an array of Geiger mode avalanche photodiodes (APDs). The sensor tiles are electronically connected to application specific integrated circuitry (ASICs) that is responsible for digitizing and pre-processing photon detection events. The circuitry may support functions such as pixel identification, time-stamping, photon counting, digital biasing, digital triggering, readout, and other functions used in PET imaging with or without time-of-flight or depth-of-interaction information (cf. below). The scintillator crystals are selected to provide high stopping power for the incident gamma radiation with a rapid temporal decay of the scintillation burst. Some suitable materials include LSO, LYSO, MLS, LGSO, LaBr, CsI(Ti), and mixtures thereof. However, it is noted that also other scintillator materials may be used. The sensor tiles are selected to have high gain and stability and to be low cost and to require a low operating voltage. Suitable sensor tiles include both analog and digital SiPMs.

In conventional PET imaging, substantially simultaneous 511 keV gamma ray detection events are defined as two 511 keV gamma ray detection events occurring within a selected short time window, such as within four nanoseconds, of each other. This short time window takes into account that any positron-electron annihilation event that does not occur at the center of the imaging region 11 will result in a small difference in time of arrival, proportional to the travel times of the two emitted 511 keV gamma rays, at the opposing PET data detection devices 31. A related technique, called time-of-flight PET (TOF-PET) imaging, takes advantage of this small time difference to further localize the positron-electron annihilation event along the LOR with sub-nanosecond precision. Another related technique, called depth-of-interaction PET (DOI-PET) imaging, makes use of multi-layered PET data detector devices to be able to determine the depth of a scintillation event within a scintillation crystal.

The PET data detection devices 31 of the PET apparatus 30 are used to acquire PET data (in the following, the term "PET data" may also include TOF-PET data and/or DOI-PET data). A coincidence detection unit 32 employs temporal windowing to identify 511 keV gamma ray detection events that occurred substantially simultaneously, and, hence, are likely to correspond to the same positron-electron annihilation event, and, hence, define a projection line or line of response (LOR). For TOF processing, the small time difference between the identified substantially simultaneous 511 keV gamma ray detection events is used to spatially estimate the positron-electron annihilation event along the LOR. Likewise, for DOI processing, the necessary depth of interaction information is retrieved. A PET image reconstruction unit 33 then reconstructs the PET data into a reconstructed PET image using a suitable image reconstruction algorithm. For example, a maximum-likelihood expectation maximization (ML-EM) algorithm, a filtered back-projection (FB) algorithm, or an iterative image reconstruction algorithm other than ML-EM may be employed. The reconstructed PET image is suitably displayed on the display unit 14, for example, by means of a suitable two- or three-dimensional rendering method, or may be otherwise processed.

In the imaging apparatus 10 of this embodiment, the PET data detection devices 31 do not continuously encircle the imaging region 11. Such incomplete encirclement can lead to imaging artifacts due to "missing" projections or lines of response (LORs). For example, certain projections can be missed, such that information ordinarily provided by such projections about related positions is unavailable. Advantageously, if TOF-PET data are acquired and reconstructed, then the time-of-flight localization provides additional information that can be used to compensate for lost information even in the presence of an incomplete encirclement. In addition, other ways of compensating for an incomplete encirclement are known to those skilled in the art in practicing the claimed invention. In other embodiments, the imaging region 11 can also be continuously encircled by the PET data detection devices 31, for example, by providing a larger number of these devices, by making use of devices having a larger spatial extend, or by positioning the devices closer to the imaging region 11.

The acquisition of the MRI and PET data may be performed sequentially (e.g., MRI first, followed by PET, or vice versa) or may be interleaved. Preferentially, however, the MRI and PET data are acquired simultaneously. This allows for simultaneous dynamic studies of different parameters, such as diffusion and perfusion, to gain new diagnostic information. In addition, it also enables an enhanced PET image reconstruction, for example, by correcting the acquired PET data for the effects of movements of the imaging subject 12, for example, a human patient, because global and local motion of a body can be tracked efficiently by means of MRI. However, in order to realize these benefits, one must be able to temporally relate the data acquired by the two different imaging modalities.

Figure 2:
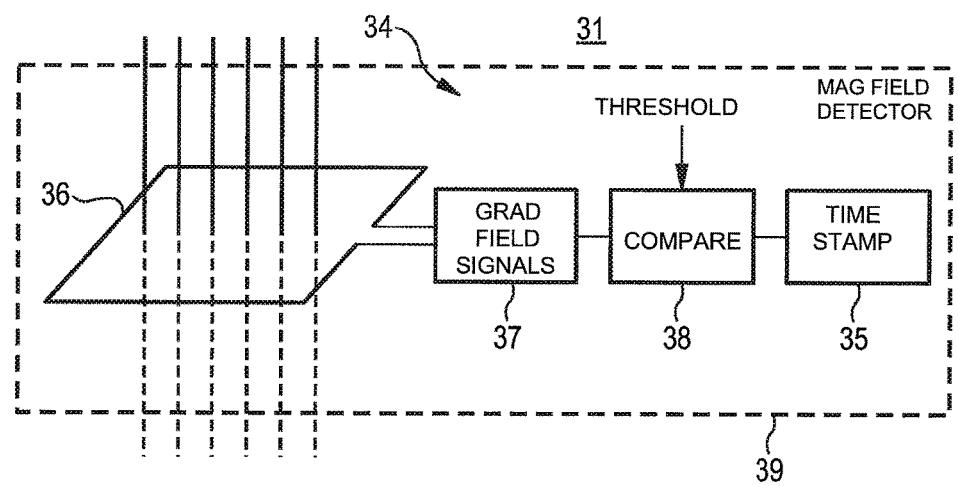
FIG. 2 shows schematically and exemplarily components of a PET data detection device.

To this end, at least one of the PET data detection devices 31 comprises a magnetic field detection unit that serves to detect a temporally varying magnetic field that is generated by the MRI apparatus 20, and a timestamping unit that generates magnetic field detection timestamps in dependence of the detected temporally varying magnetic field (cf. FIG. 2). Since the temporal variations of the switched magnetic field gradients and of the pulse RF magnetic field $B_1$ inherently provide information about the times at which the MRI apparatus 20 acquires MRI data (i.e., the "MRI acquisition timing"), it is possible for the PET data detection device 31, by means of the above configuration, to determine, in a relatively simple manner, and, in particular, without the need for a special, dedicated interface between the PET data detection device 31 and the MRI apparatus 20, a temporal relation to the acquired MRI data.

A suitable magnetic field detection unit 34 and a timestamping unit 35 are described in more detail with reference to FIG. 2, which shows schematically and exemplarily a PET data detection device 31 comprising inter alia these two components.

Figure 3:
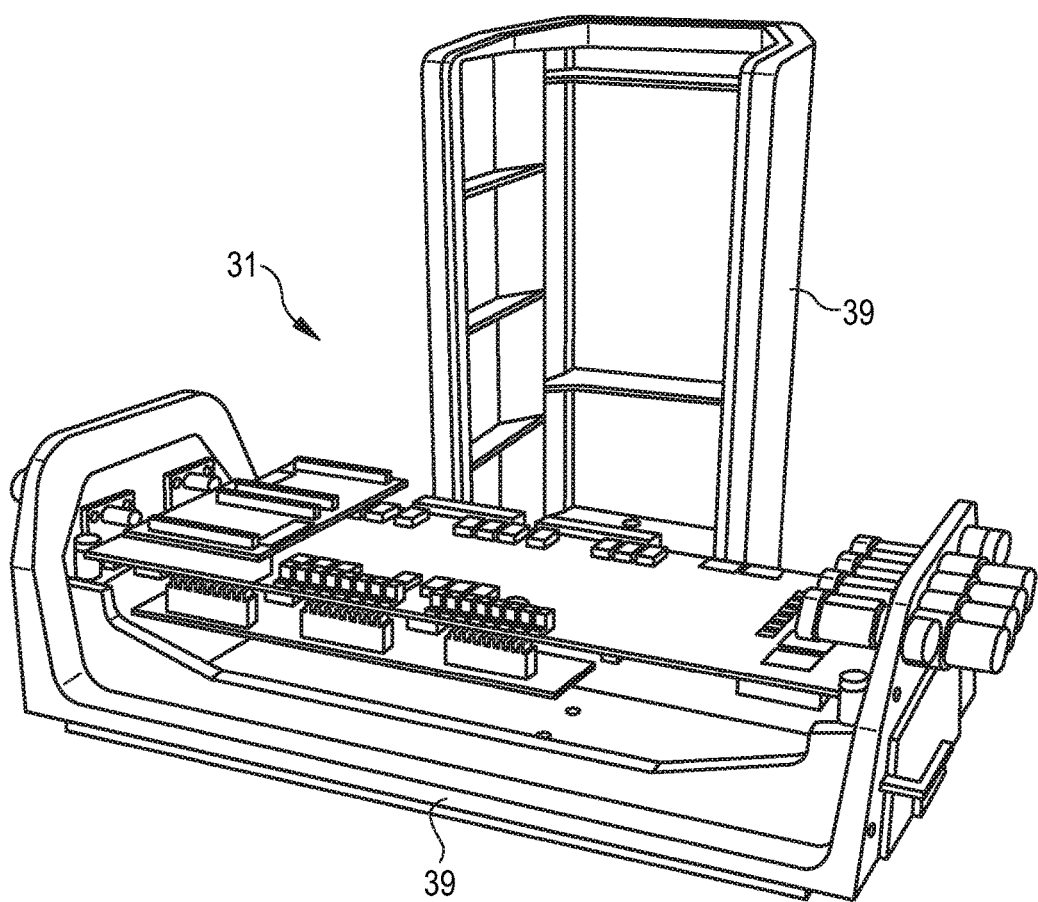
FIG. 3 shows schematically and exemplarily a radio frequency shield housing the electronics of a PET data detection device.

The magnetic field detection unit 34, in this embodiment, comprises a coil 36 that serves to provide electric currents that are induced by temporal variations of the temporally varying magnetic field. (The temporally varying magnetic field is illustrated by the vertical lines that pass through the coil 36.) As described above, the temporally varying magnetic field that is to be detected by the magnetic field detection unit 34 can be the pulse RF magnetic field $B_1$ generated, for example, by the RF coil 23 of the MRI apparatus 20, or it can be a switched magnetic field gradient generated by the magnetic field gradient coils 22 of the MRI apparatus 20. Here, the later option is realized and the PET data detection device 31 further comprises a radio frequency shield 39 that serves to shield the magnetic field detection unit 34 from the pulse RF magnetic field $B_1$ generated by the MRI apparatus 20 (for example, by the RF coil 23). In this embodiment, the radio frequency shield 39 is made from a material with suitable RF shielding characteristics, such as copper or carbon, and also houses the electronics of the PET data detection device 31, as is shown schematically and exemplarily in FIG. 3. This configuration ensures, on the one hand, that the PET electronics, including the magnetic field detection unit 34, are not influenced or disturbed by the pulse RF magnetic field $B_1$ and, on the other hand, that electronic noise from the PET electronics also does not influence or disturb the electronics of the MRI apparatus 20. While the radio frequency shield 39 is substantially impenetrable for the high frequencies of the pulse RF magnetic field $B_1$ (which typically are in the range of about 100 MHz), the switched magnetic field gradients (which typically vary in the kHz-range) penetrate the radio frequency shield 39 due to their lower frequencies and, because their frequencies are not too low, induce electric currents in the PET electronics. (By way of comparison, the static magnetic field $B_0$ also penetrates the radio frequency shield 39, but, because of its temporally uniform nature, does not induce electric currents in the PET electronics.)

The electric currents that are induced by the switched magnetic field gradients in the PET electronics are normally regarded as a problem in combined PET/MRI imaging apparatuses and various measures, such as shortening transmission lines as much as possible or utilizing twisted differential pair lines, are typically performed to reduce and/or compensate their influence on the acquisition and processing of the PET data. On the other hand, by providing a coil 36 in a magnetic field detection unit 34 as described above, the electric currents that are induced in the coil 36 by a switched magnetic field gradient can also be used advantageously as a basis for generating the magnetic field detection timestamps. To this end, the magnetic field detection unit 34 comprises a signal providing unit 37 that serves to provide signals in dependence of the provided electric currents, wherein the timestamping unit 35 is adapted to generate the magnetic field detection timestamps in dependence of the provided signals. In this embodiment, the magnetic field detection unit 34 further comprises a signal comparison unit 38 that serves to compare the provided signals to a specified signal threshold, and the timestamping unit 35 is adapted to generate the magnetic field detection timestamps when the provided signals cross the specified signal threshold. It is noted that the term "cross" as used herein is intended to be interpreted broadly, wherein its meaning depends on the characteristic of the provided signals, i.e., on the relationship between the induced electric currents resulting from the temporal variations of the temporally varying magnetic field and the provided signals. For example, if a default "base" signal is provided by the signal providing unit 37 in the case where no induced electric currents are provided by the coil 36 and if the induced electric currents result in a reduction of the provided default "base" signal, the meaning of the term "cross" also includes the case that the provided signals fall below a specified signal threshold that is smaller than the default "base" signal.

The magnetic field detection unit 34 may be realized, for example, by utilizing suitable analog and/or digital comparator electronics. In one realization, the signal providing unit 37 provides as the signals electric voltages that depend on the induced electric currents provided by the coil 36. The electric voltages may be derived from an electric supply voltage that is "modulated" with an electric voltage resulting from a voltage drop across a resistor upon a flow of electric current in the coil 36. The electric voltages are then provided to the signal comparison unit 38, which may comprise, for example, a dedicated comparator or an operational amplifier (op-amp) used as a comparator or the like, where they are compared with a specified signal threshold, in this case, a specified electric voltage. If an electric voltage provided by the signal providing unit 37 (i.e., a signal) is larger than the specified electric voltage (i.e., the specified signal threshold), a digital pulse is generated to indicate that a temporal variation of a switched magnetic field gradient was identified and the timestamping unit 35 generates a magnetic field detection timestamp. It should be noted that other realizations of the signal providing unit 37 and/or of the signal comparison unit 38 are also possible and may be utilized by a person skilled in the art in practicing the claimed invention. For example, the signal providing unit 37 may provide as the signals electric currents or other suitable parameters and the signal processing may be either analog or digital or may be based on a combination thereof.

The switched magnetic field gradients generated by the magnetic field gradient coils 22 of the MRI apparatus 20 do no only vary with time but also vary with position in space. Moreover, respective MR pulse sequences may differ in a number of parameters, such as the maximum strength and/or the switching slope (i.e., the change of strength per time interval) of the switched magnetic field gradients. For a reliable detection, it is therefore preferred that the sensitivity of detecting the temporally varying magnetic field, here, a switched magnetic field gradient, can be adjusted to fit the respective circumstances. In this embodiment, this is realized by the signal comparison unit 38 being adapted to enable an adjustment of the specified signal threshold (illustrated by the arrow in FIG. 2), i.e., the specified signal threshold may be suitably increased or decreased. Since the law of induction states that induction is proportional to the rate of change of a magnetic field through the area of a coil, the electric currents that are induced by a switched magnetic field gradient in the coil 36 depend both on the position and/or orientation of the PET data detection device 31, in particular, of the coil 36, relative to the switched magnetic field gradient and on the parameters of the respective MR pulse sequence. By adjusting the specified signal threshold according to need, the combined effect of these different parameters can be suitably taken into account.

Preferably, the specified signal threshold will be adjusted such that the magnetic field detection unit 34 will not falsely react on noise or any other unwanted signal. A value just above the noise level will allow detection of as much temporal variations of a switched magnetic field gradient as possible. In one embodiment, a PET data detection device 31 comprising a magnetic field detection unit 34 may be positioned within the MRI apparatus 20 in a region where the switched magnetic field gradient in the x direction (denoted "$G_x$" by convention) is particularly strong, and the magnetic field detection unit 34 may be adjusted to "trigger" on temporal variations of the switched magnetic field gradient $G_x$. In another embodiment, an additional or an alternative PET data detection device 31 comprising a magnetic field detection unit 34 may be positioned within the MRI apparatus 20 in a region where the switched magnetic field gradient in the y direction (denoted "$G_y$" by convention) is particularly strong, and the magnetic field detection unit 34 may be adjusted to "trigger" on temporal variations of the switched magnetic field gradient $G_y$. Of course, other embodiments are also conceivable. For example, in the imaging system 10 shown in FIG. 1, the twelve PET data detection devices 31 may each comprise a magnetic field detection unit 34 and the respective detection results may be logically combined in a most suitable manner in order to increase detection reliability. Moreover, a magnetic field detection unit 34 may be adapted to only "trigger" on certain temporal variations of a switched magnetic field gradient, e.g., only on the respective build-up of the switched magnetic field gradient.

Figure 4:
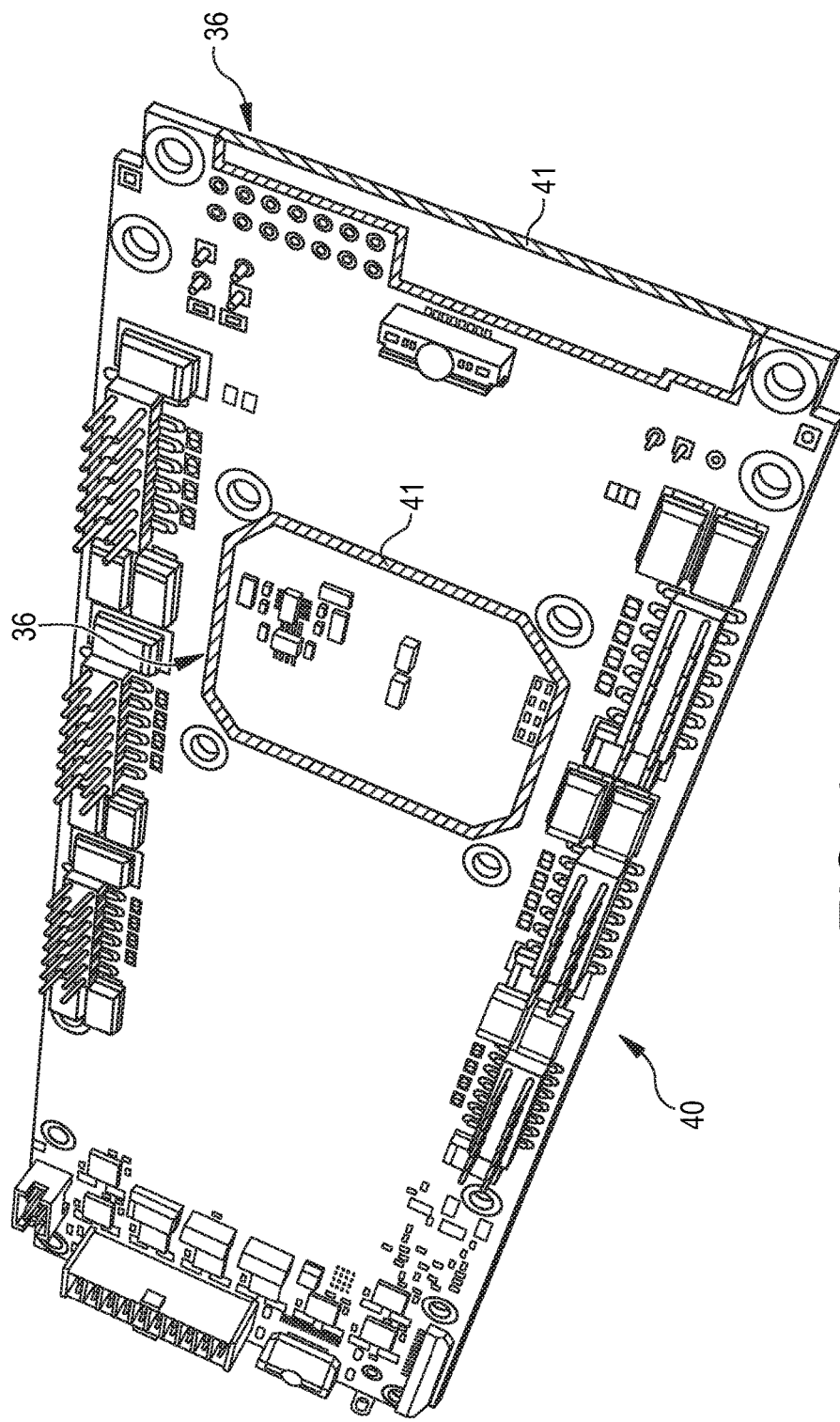
FIG. 4 shows schematically and exemplarily a printed circuit board (PCB) comprised by a PET data detection device.

The coil 36 can be realized in the magnetic field detection unit 34 by different means. For example, the PET data detection device 31 of this embodiment comprises a printed circuit board (PCB) 40, as is shown schematically and exemplarily in FIG. 4. On the PCB, different components of the PET electronics are realized. In this embodiment, two coils 36 that are substantially made from PCB traces 41 are provided, but a coil 36 can also comprise an air-core inductor that can, for example, be soldered to the PCB. A first coil 36, shown on the right side of the figure at the margin of the PCB, extends on both the front- and the backside of the PCB, thereby providing a loop that is suitably oriented for detecting the switched magnetic field gradients generated by the MRI apparatus 20 when the PET data detection device 31 is positioned within the imaging system 10 as shown in FIG. 1. (The switched magnetic field gradients are generally aligned with the static magnetic field $B_0$, i.e., they extend in the z direction.) A second coil 36, shown on the frontside of the PCB, is arranged to be (substantially) perpendicular to the first coil 36 and may be used to detect "stray" components of the switched magnetic field gradients perpendicular to the static magnetic field $B_0$. Such "stray" components are usually unwanted, but may occur in the MRI apparatus 20 because a magnetic field gradient system can never be 100% ideal. If a third coil 36 (not shown) is arranged to be (substantially) perpendicular to both the first and second coil 36 and if this third coil 36 is also used to detect such "stray" components, the information provided by the three (substantially) perpendicularly arranged coils 36 can be used to determine the positioning and/or the orientation of the PET data detection device relative to the switched magnetic field gradients —provided that sufficient knowledge about the characteristics of the "stray" components generated by the MRI apparatus 20 is available, e.g. from earlier measurements.

The timestamping unit 35 is adapted to generate the magnetic field detection timestamps in accordance with a common time base that is also utilized for generating data timestamps for data detected by the PET data detection device 31. In this embodiment, the twelve PET data detection devices 31 shown in FIG. 1 each comprise an interface for receiving timing information from a common system clock of the PET apparatus 30 (not shown) to facilitate consistent timestamping of 511 keV gamma ray detection events (i.e., to consistently generate data timestamps for detected PET data) in the twelve PET data detection devices 31. The timestamping unit 35 makes use of the same timing information from the common system clock to generate the magnetic field detection timestamps. Here, the generated magnetic field detection timestamps are stored with other PET "metadata", such as device temperatures, et cetera.

As described above, the magnetic field detection timestamps generated by the magnetic field detection unit provide a temporal relation to the acquired MRI data that enables an enhanced PET image reconstruction. For example, if the PET acquisition is started earlier than the MRI acquisition (which usually is the case because of the longer time required for acquiring PET data), the generated magnetic field detection timestamps provide the necessary information for determining when the MRI acquisition was started relative to the PET acquisition. Moreover, it is possible to temporally relate individual reconstructed MRI images to acquired PET data.

Figure 5:
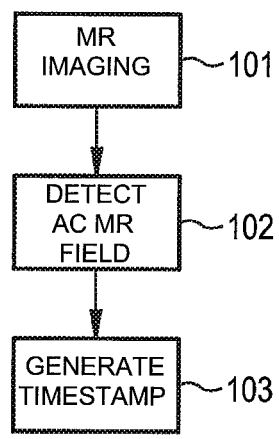
FIG. 5 shows a flowchart exemplarily illustrating an embodiment of an imaging method.

In the following, an imaging method will be described with reference to a flowchart shown in FIG. 5.

In step 101, magnetic resonance imaging (MRI) is performed. In addition, data detection, in this embodiment, PET data detection is performed, wherein, in step 102, a temporally varying magnetic field generated by the MRI method is detected, and wherein, in step 103, magnetic field detection timestamps are generated in dependence of the detected temporally varying magnetic field. Here, the temporally varying magnetic field is detected by a magnetic field detection unit 34 and the magnetic field detection timestamps are generated by a timestamping unit 35. An embodiment of such components is shown, schematically and exemplarily, in FIG. 2.

Steps 102 and 103 can be regarded as being steps of a data detection method for use in combination with a magnetic resonance imaging (MRI) method.

In the embodiments described above, the data detection device for use in combination with a magnetic resonance imaging (MRI) apparatus is a positron emission tomography (PET) data detection device, but it can also be another type of nuclear data detection device, such as a single photon emission computed tomography (SPECT) data detection device, or it can be, for example, an ultrasound data detection device, or any other data detection device that may suitably be used in combination with an MRI apparatus and that can benefit from the ability to determine a temporal relation to acquired MRI data. In particular, the data detection device can also be a device that is provided for medical purposes other than imaging, for example, it can be a device for detecting one ore more vital parameters of a patient.

The magnetic field detection unit can, in some embodiments, also utilize a Hall effect sensor or a comparable device to detect a temporally varying magnetic field generated by a magnetic resonance imaging (MRI) apparatus. Other embodiments can even be based on utilizing the orientation of elements that align themselves along the lines of a magnetic field or on similar, compass-type effects.

It is possible that the magnetic field detection unit is adjusted, for example, by a suitable adjustment of the specified signal threshold(s), such that it only detects particularly strong temporal variations of the temporally varying magnetic field, which may appear in a respective MR pulse sequence only at specific temporal positions. This may minimize the amount of redundant data to be processed. It is also thinkable that such particularly strong temporal variations of the temporally varying magnetic field (which may not be used by the MRI imaging process) are explicitly incorporated in an MR pulse sequence, e.g., at any one time before an MRI image is taken, or before a navigator is measured, for the purpose of detection by the magnetic field detection unit.

It is also conceivable that in the magnetic field detection unit, a coil or another component that is sensitive to a temporally varying magnetic field is orientably positioned. This may allow to orient the coil or other component in the most suitable manner, e.g., in such a way that it is most sensitive to the temporally varying magnetic field, depending on the position and/or orientation of the data detection device relative to the temporally varying magnetic field. For example, the coil or other component may be installed on a joint or pivot that allows a change in orientation in at least one dimension, preferentially, in all three dimensions.

As described above, it is possible that the temporally varying magnetic field to be detected by the magnetic field detection unit is the pulse RF magnetic field $B_1$. In the case where the data detection device is a PET data detection device or another device with comparable sensitive electronics, the electronics may nonetheless be housed in a radio frequency shield made from a material with suitable RF shielding characteristics, such as copper or carbon, but the magnetic field detection unit, resp., if applicable, at least the coil or other component that is sensitive to the pulse RF magnetic field $B_1$ may be provided outside the radio frequency shield.

In some embodiments, the magnetic field detection unit can comprise, for example, at least three substantially parallel oriented coils that are arranged in a triangle extending in each of the x, y, and z directions. By making use of knowledge about the spatially varying nature of the switched magnetic field gradients generated by the MRI apparatus, e.g., by knowing their maximum strength and their switching slope, it is therewith possible to determine, from the induced electric currents provided by the at least three substantially parallel oriented coils, the position and/or the orientation of the data detection device.

In the embodiments described above, the temporally varying magnetic field to be detected by the magnetic field detection unit is a switched magnetic field gradient and the electronics of the PET data detection device are housed in a radio frequency shield made from a material with suitable RF shielding characteristics, such as copper or carbon. If such an RF shielding is not utilized, it is possible to reduce and/or compensate the influence of the pulse RF magnetic field $B_1$ on the detection of the switched magnetic field gradient by means of suitable filter techniques.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the detecting of a temporally varying magnetic field, the generating of magnetic field detection timestamps, et cetera performed by one or several units or devices can be performed by any number of units or devices. For example, steps like the providing of electric currents induced by temporal variations of the temporally varying magnetic field and the providing of signals in dependence of the provided electric currents can be performed by a single unit, by two different units, or by any other number of different units. These operations and/or the control of the data detection device in accordance with the data detection method and/or the control of the imaging apparatus in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A data detection device configured for use in combination with both a nuclear imaging apparatus and a magnetic resonance imaging (MRI) apparatus, the data detection device comprising:
   nuclear detector electronics configured to detect nuclear radiation and generate nuclear image data;
   wherein the nuclear detector of the nuclear detector electronics, is one of a positron emission tomography (PET) detector device or a single photon emission computed tomography (SPECT) detector device;
   a magnetic field detector configured to detect a temporally varying magnetic field generated by the MRI apparatus, wherein the magnetic field detector is mounted with the nuclear detector electronics; and
      a timestamping unit configured to generate timestamps for at least the nuclear data that are based on a common clock and the detected temporally varying magnetic field that was generated by the MRI apparatus.

2. The data detection device as defined in claim 1, wherein the magnetic field detector comprises:
   at least one coil in which electric currents are induced by temporal variations of the temporally varying magnetic field; and wherein the timestamping unit is further configured to generate the magnetic field detection timestamps based on and in dependence of the induced electric currents.

3. The data detection device as defined in claim 2, wherein the magnetic field detector further comprises:
a comparator that is configured to compare the induced electric currents to a specified signal-threshold,
wherein the timestamping unit is further configured to generate the magnetic field detection timestamps when an amplitude of the induced currents crosses the specified signal-threshold.

4. The data detection device as defined in claim 3, wherein the magnetic field detection unit is configured to have an adjustable specified signal-threshold.

5. A combined imaging apparatus, comprising:
a magnetic resonance imaging (MRI) apparatus:
a nuclear imaging system configured with a common imaging region, and
the data detection device as defined in claim 1.

6. The data detection device as defined in claim 2 wherein the magnetic field detector includes three coils that are arranged to be perpendicular to each other and configured to generate signals that are indicative of a position of the magnetic field detector.

7. The data detection device as defined in claim 4, wherein the specified signal threshold is adjusted in order to appropriately detect the magnetic field variations occurring in a switched magnetic field gradient generated by the MRI apparatus.

8. The data detection device as defined in claim 1, further comprising:
a radio frequency shield configured to shield the magnetic detector from a pulsed radio frequency (RF) magnetic field B1 generated by the MRI apparatus, without shielding the magnetic detector from the lower frequency magnetic field variations, that are attributable to gradient magnetic fields generated by the MRI apparatus.

9. The data detection device as defined in claim 8, wherein the radio frequency shield is further configured to shield the MRI apparatus and the magnetic field detector, from stray signals being emitted by, or emanating from the nuclear detector that is is one of a positron emission tomography (PET) detector device or a single photon emission computed tomography (SPECT) detector device.

10. A data detection device configured for use in combination with a magnetic resonance imaging (MRI) apparatus, the data detection device comprising:
at least one coil configured to provide electric currents induced by temporal variations of a detected temporally varying magnetic field generated by the MRI apparatus;
a printed circuit board (PCB), wherein the at least one coil is made substantially from PCB traces or a PCB upon which the at least one coil comprises an air-core inductor; and
a timestamping unit configured to generate magnetic field detection timestamps in dependence of the electric currents induced by the detected temporally varying magnetic field.

11. A data detection method that is utilized in combination with a combined nuclear imaging and magnetic resonance imaging (MRI) method, the data detection method comprising the steps of:
concurrently collecting nuclear imaging data with a nuclear detector that is one of a positron emission tomography (PET) detector device or a single photon emission computed tomography (SPECT) detector device, and collecting MRI data with at least one coil of a magnetic resonance imaging apparatus, from a common imaging region;
detecting at least one temporally varying magnetic field, generated by the combined nuclear imaging and MRI method with a magnetic field detection unit;
generating timestamps of at least the collected nuclear imaging data based on a common clock in dependence of the detected at least one temporally varying magnetic field with a timestamping unit when the detected data signals cross a predetermined threshold: and
timestamping at least the collected nuclear imaging data with the generated time stamps by utilizing the timestamping unit to perform the timestamping step when the detected data signals cross the said predetermined threshold.

12. A data detection method that is utilized in combination with a combined nuclear imaging and magnetic resonance imaging (MRI) method as defined in claim 11 further including:
reconstructing, with an image reconstruction unit, the timestamped nuclear imaging data and the collected MRI data, into a combined nuclear and magnetic resonance image of an examination subject within the common imaging region that is then provided, or displayed, as an output of performing this combined nuclear imaging and magnetic resonance imaging (MRI) data detection method.

13. A non-transitory computer-readable medium carrying software configured for controlling one or more processors in order to control an imaging system that performs the method of claim 12 which combines a nuclear imaging and magnetic resonance imaging (MRI) data detection method, when the non-transitory computer-readable medium software is executed.

* * * * *